United States Patent
Olsen et al.

(12) 
(10) Patent No.: US 6,284,486 B1
(45) Date of Patent: Sep. 4, 2001

(54) HUMAN ONCOGENE INDUCED SECRETED PROTEIN I

(75) Inventors: Henrik S. Olsen, Gaithersburg; Steven M. Ruben, Olney, both of MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 08/994,962

(22) Filed: Dec. 19, 1997

Related U.S. Application Data

(60) Provisional application No. 60/033,869, filed on Dec. 20, 1996, and provisional application No. 60/037,388, filed on Feb. 7, 1997.

(51) Int. Cl.⁷ ................................................. C12P 21/06
(52) U.S. Cl. .................. 435/69.1; 435/91.1; 435/91.4; 435/91.41; 435/252.3; 435/6; 536/23.1; 536/23.5; 536/24.1; 536/24.2
(58) Field of Search ................... 435/69.1, 91.1, 435/91.4, 91.41, 252.3, 320.1, 6; 536/23.1, 23.5, 24.1, 24.2

(56) References Cited

FOREIGN PATENT DOCUMENTS

WO 91/00292 * 10/1991 (WO).
WO 90/18205   4/1999 (WO).

OTHER PUBLICATIONS

Database GenBank on STN, Hudson, T., Accession No. G26160, Jun. 2, 1996.*
Database GenBank on STN, Chang et al., Accession No. R10399, Apr. 9, 1991.*
Begum, N.A., et al., "Human MD–1 Homologue Is a BCG–Regulated Gene Product in Monocytes: Its Identification by Differential Display," *Biochem. Biophys. Res. Commun.* 256:325–329, Academic Press, Inc., Orlando, FL (1999).
Miyake, K., et al., "Mouse MD-1, a Molecule That Is Physically Associated with RP105 and Positively Regulates Its Expression," *J. Immunol.* 161:1348–1353, American Association of Immunologists, Baltimore, MD (1998).
Burk, O. and K.–H. Klempnauer, "Estrogen–dependent alterations in differentiation state of myeloid cells caused by a v–myb/estrogen receptor fusion protein,"*EMBO J.* 10(12):3713–3719 (1991).
Golay, J. et al., "A Single Point Mutation in the v–ets Oncogene Affects Both Erythroid and Myelomonocytic Cell Differentiation," *Cell* 55:1147–1158 (1988).
Introna, M. et al., "Mutations in v–myb Alter the Differentiation of Myelomonocytic Cells Transformed by the Oncogene," *Cell* 63: 1287–1297 (1990).
Klempnauer, K.–H. et al., "Subcellular Localization of Proteins Encoded by Oncogenes of Avian Myeloblastosis Virus and Avian Leukemia Virus E26 and by the Chicken c–myb Gene," *Cell* 37:537–547 (1984).
Mosovici, C. and L. Gazzolo, "Transformation of Hemopoietic Cells with Avian Leukemia Viruses," *Adv. in Virol Oncol.* 1:83–106 (1982).
Ness, S.A. et al., "The v–myb Oncogene Product Binds to and Activates the Promyelocyte–Specific mim–1 Gene," *Cell* 59:1115–1125 (1989).
Quéva, C. et al., "Expression patterns of c–myb and v–myb induced myeloid–1 (min–1) gene during the development of the chick embryo," *Develop.* 114:125–133 (1992).
Genbank report, Accession No. T84854, submitted by Hillier, L. et al. (Mar. 1995).
Genbank report, Accession No. T91708, submitted by Hillier, L. et al. (Mar. 1995).
Genbank report, Accession No. T92475, submitted by Hillier, L. et al. (Mar. 1995).
Genbank report, Accession No. C02431, submitted by Okubo, K. (Jul. 1996).
Genbank report, Accession No. AA340310, submitted by Adams, M.D. et al. (Apr. 1997).
GenBank report, Accession No. AA688404, submitted by NCI–CGAP (Dec. 1997).

* cited by examiner

*Primary Examiner*—Karen Cochrane Carlson
(74) *Attorney, Agent, or Firm*—Sterne, Kessler, Goldstein & Fox P.L.L.C.

(57) ABSTRACT

The present invention relates to a novel protein, the Human Oncogene Induced Secreted Protein I ("HOIPS I") protein. In particular, isolated nucleic acid molecules are provided encoding the human HOIPS I protein. HOIPS I polypeptides are also provided as are vectors, host cells and recombinant methods for producing the same. Also provided are diagnostic methods for detecting abnormal cell proliferation and differentiation disorders and therapeutic methods for treating the same.

69 Claims, 4 Drawing Sheets

```
      TCCCATACAGGCCCCCACCATGAAGGGTTTCACAGCCACTCTCTTCCTCTGGACTCTGAT
   1  ----------+----------+----------+----------+----------+----------+  60
                       MetLysGlyPheThrAlaThrLeuPheLeuTrpThrLeuIl
   1                    M   K   G   F   T   A   T   L   F   L   W   T   L   I   14

TTTTCCCAGCTGCAGTGGAGGCGGCGGTGGGAAAGCCTGGCCCACACACGTGGTCTGTAG
  61  ----------+----------+----------+----------+----------+----------+ 120
      ePheProSerCysSerGlyGlyGlyGlyGlyLysAlaTrpProThrHisValValCysSe
  15   F   P   S   C   S   G   G   G   G   G   K   A   W   P   T   H   V   V   C   S   34

CGACAGCGGCTTGGAAGTGCTCTACCAGAGTTGCGATCCATTACAAGATTTTGGCTTTTC
 121  ----------+----------+----------+----------+----------+----------+ 180
      rAspSerGlyLeuGluValLeuTyrGlnSerCysAspProLeuGlnAspPheGlyPheSe
  35   D   S   G   L   E   V   L   Y   Q   S   C   D   P   L   Q   D   F   G   F   S   54

TGTTGAAAAGTGTTCCAAGCAATTAAAATCAAATATCAACATTAGATTTGGAATTATTCT
 181  ----------+----------+----------+----------+----------+----------+ 240
      rValGluLysCysSerLysGlnLeuLysSerAsnIleAsnIleArgPheGlyIleIleLe
  55   V   E   K   C   S   K   Q   L   K   S   N   I   N   I   R   F   G   I   I   L   74

GAGAGAGGACATCAAAGAGCTTTTTCTTGACCTAGCTCTCATGTCTCAAGGCTCATCTGT
 241  ----------+----------+----------+----------+----------+----------+ 300
      uArgGluAspIleLysGluLeuPheLeuAspLeuAlaLeuMetSerGlnGlySerSerVa
  75   R   E   D   I   K   E   L   F   L   D   L   A   L   M   S   Q   G   S   S   V   94

TTTGAATTTCTCCTATCCCATCTGTGAGGCGGCTCTGCCCAAGTTTTCTTTCTGTGGAAG
 301  ----------+----------+----------+----------+----------+----------+ 360
      lLeuAsnPheSerTyrProIleCysGluAlaAlaLeuProLysPheSerPheCysGlyAr
  95   L   N   F   S   Y   P   I   C   E   A   A   L   P   K   F   S   F   C   G   R   114

AAGGAAAGGAGAGCAGATTTACTATGCTGGGCCTGTCAATAATCCTGAATTTACTATTCC
 361  ----------+----------+----------+----------+----------+----------+ 420
      gArgLysGlyGluGlnIleTyrTyrAlaGlyProValAsnAsnProGluPheThrIlePr
 115   R   K   G   E   Q   I   Y   Y   A   G   P   V   N   N   P   E   F   T   I   P   134

TCAGGGAGAATACCAGGTTTTGCTGGAACTGTACACTGAAAAACGGTCCACCGTGGCCTG
 421  ----------+----------+----------+----------+----------+----------+ 480
      oGlnGlyGluTyrGlnValLeuLeuGluLeuTyrThrGluLysArgSerThrValAlaCy
 135   Q   G   E   Y   Q   V   L   L   E   L   Y   T   E   K   R   S   T   V   A   C   154

TGCCAATGCTACTATCATGTGCTCCTGACTGTGGCCTGTAGCAAAAATCACAGCCAGCTG
 481  ----------+----------+----------+----------+----------+----------+ 540
      sAlaAsnAlaThrIleMetCysSerEnd
 155   A   N   A   T   I   M   C   S   *                                 162

CATCTCGTGGGACCTCCAAGCTCCTCTGACTGAACCTACTGTGGGAGGAGAAGCAGCTGA
 541  ----------+----------+----------+----------+----------+----------+ 600
```

FIG.1A

```
     TGACAGAGAGAGGCTCTACAAAGAAGCGCCCCCAAAGAGTGCAGCTGCTAATTTTAGTCC
601  ---------+---------+---------+---------+---------+---------+  660

CAGGACCAGACATCCCCAGACTCCACAGATGTAATGAAGTCCCCGAATGTATCTGTTTCT
661  ---------+---------+---------+---------+---------+---------+  720

AAGGAGCCTCTTGGCAGTCCTTAAGCAGTCTTGAGGGTCCATCCTTTTTCTCTAATTGGT
721  ---------+---------+---------+---------+---------+---------+  780

CGCCTCCCACCAGACTCACCTGCTTTTCAACTTTTTAGGAGTGCTTCCTCACAGTTACCA
781  ---------+---------+---------+---------+---------+---------+  840

AGAAATAAAGAAAGCTGGCC
841  ---------+---------+  860
```

Nucleotide sequence of Human MD-1 Homolog. Corresponding deduced amino-acid sequence shown below using standard three and one letter abbreviation.

FIG.1B

Score = 344 (160.0 bits), Expect = 6.6e-44, P = 6.6e-44
Identities = 60/133 (45%), Positives = 86/133 (64%)

```
Query:   27 WPTHVVCSDSGLEVLYQSCDPLQDFGFSVEKCSKQLKSNINIRFGIILREDIKELFLDLA  86
            WPTH VC +  LE+ Y+SCDP QDF FS+++CS      +IR ++LR+ IKEL+ +
Sbjct:   22 WPTHTVCKEENLEIYYKSCDPQQDFAFSIDRCSDVTTHTFDIRAAMVLRQSIKELYAKVD  81

Query:   87 LMSQGSSVLNFSYPICEAALPKFSFCGRRKGEQIYYAGPVNNPEFTIPQGEYQVLLKLYT 146
            L+  G +VL++S +C   L K  FCG++KGE +YY GP+       IPQG+Y + L
Sbjct:   62 LIINGKTVLSYSETLCGPGLSKLIFCGKKKGEHLYYEGPITLGIKEIPQGDYTITARLTN 141

Query:  147 EKRSTVACANATI 159
            E R+TVACA+ T+
Sbjct:  142 EDRATVACADFTV 154
```

Sequence comparison between human MD-1 protein (upper line) and MD-1 protein from chicken (lower line).

FIG.2 under the heading "HUMAN ONCOGENE INDUCED SECRETED PROTEIN I"...

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 860 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 20..505

(ix) FEATURE:
      (A) NAME/KEY: sig_peptide
      (B) LOCATION: 20..79

(ix) FEATURE:
      (A) NAME/KEY: mat_peptide
      (B) LOCATION: 80..505

(xi) SEQUENCE DESCRIPTION: SEQ ID NO:1:

```
TCCCATACAG GCCCCCACC ATG AAG GGT TTC ACA GCC ACT CTC TTC CTC TGG        52
                     Met Lys Gly Phe Thr Ala Thr Leu Phe Leu Trp
                     -20             -15                 -10

ACT CTG ATT TTT CCC AGC TGC AGT GGA GGC GGC GGT GGG AAA GCC TGG        100
Thr Leu Ile Phe Pro Ser Cys Ser Gly Gly Gly Gly Gly Lys Ala Trp
         -5                  1                   5
```

-continued

| | | |
|---|---|---|
| CCC ACA CAC GTG GTC TGT AGC GAC AGC GGC TTG GAA GTG CTC TAC CAG<br>Pro Thr His Val Val Cys Ser Asp Ser Gly Leu Glu Val Leu Tyr Gln<br>          10                    15                    20 | | 148 |
| AGT TGC GAT CCA TTA CAA GAT TTT GGC TTT TCT GTT GAA AAG TGT TCC<br>Ser Cys Asp Pro Leu Gln Asp Phe Gly Phe Ser Val Glu Lys Cys Ser<br> 25                    30                    35 | | 196 |
| AAG CAA TTA AAA TCA AAT ATC AAC ATT AGA TTT GGA ATT ATT CTG AGA<br>Lys Gln Leu Lys Ser Asn Ile Asn Ile Arg Phe Gly Ile Ile Leu Arg<br>40                    45                    50                    55 | | 244 |
| GAG GAC ATC AAA GAG CTT TTT CTT GAC CTA GCT CTC ATG TCT CAA GGC<br>Glu Asp Ile Lys Glu Leu Phe Leu Asp Leu Ala Leu Met Ser Gln Gly<br>                    60                    65                    70 | | 292 |
| TCA TCT GTT TTG AAT TTC TCC TAT CCC ATC TGT GAG GCG GCT CTG CCC<br>Ser Ser Val Leu Asn Phe Ser Tyr Pro Ile Cys Glu Ala Ala Leu Pro<br>          75                    80                    85 | | 340 |
| AAG TTT TCT TTC TGT GGA AGA AGG AAA GGA GAG CAG ATT TAC TAT GCT<br>Lys Phe Ser Phe Cys Gly Arg Arg Lys Gly Glu Gln Ile Tyr Tyr Ala<br>          90                    95                    100 | | 388 |
| GGG CCT GTC AAT AAT CCT GAA TTT ACT ATT CCT CAG GGA GAA TAC CAG<br>Gly Pro Val Asn Asn Pro Glu Phe Thr Ile Pro Gln Gly Glu Tyr Gln<br>105                    110                    115 | | 436 |
| GTT TTG CTG GAA CTG TAC ACT GAA AAA CGG TCC ACC GTG GCC TGT GCC<br>Val Leu Leu Glu Leu Tyr Thr Glu Lys Arg Ser Thr Val Ala Cys Ala<br>120                    125                    130                    135 | | 484 |
| AAT GCT ACT ATC ATG TGC TCC TGACTGTGGC CTGTAGCAAA AATCACAGCC<br>Asn Ala Thr Ile Met Cys Ser<br>                    140 | | 535 |
| AGCTGCATCT CGTGGGACCT CCAAGCTCCT CTGACTGAAC CTACTGTGGG AGGAGAAGCA | | 595 |
| GCTGATGACA GAGAGAGGCT CTACAAAGAA GCGCCCCCAA AGAGTGCAGC TGCTAATTTT | | 655 |
| AGTCCCAGGA CCAGACATCC CCAGACTCCA CAGATGTAAT GAAGTCCCCG AATGTATCTG | | 715 |
| TTTCTAAGGA GCCTCTTGGC AGTCCTTAAG CAGTCTTGAG GGTCCATCCT TTTTCTCTAA | | 775 |
| TTGGTCGCCT CCCACCAGAC TCACCTGCTT TTCAACTTTT TAGGAGTGCT TCCTCACAGT | | 835 |
| TACCAAGAAA TAAAGAAAGC TGGCC | | 860 |

(2) INFORMATION FOR SEQ ID NO:2:

(i) SEQUENCE CHARACTERISTICS:
        (A) LENGTH: 162 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Gly Phe Thr Ala Thr Leu Phe Leu Trp Thr Leu Ile Phe Pro
-20                  -15                      -10                        -5

Ser Cys Ser Gly Gly Gly Gly Lys Ala Trp Pro Thr His Val Val
               1                    5                        10

Cys Ser Asp Ser Gly Leu Glu Val Leu Tyr Gln Ser Cys Asp Pro Leu
            15                    20                    25

Gln Asp Phe Gly Phe Ser Val Glu Lys Cys Ser Lys Gln Leu Lys Ser
      30                    35                    40

Asn Ile Asn Ile Arg Phe Gly Ile Ile Leu Arg Glu Asp Ile Lys Glu
45                    50                    55                    60

Leu Phe Leu Asp Leu Ala Leu Met Ser Gln Gly Ser Ser Val Leu Asn
            65                    70                    75

```
Phe Ser Tyr Pro Ile Cys Glu Ala Ala Leu Pro Lys Phe Ser Phe Cys
             80                  85                  90

Gly Arg Arg Lys Gly Glu Gln Ile Tyr Tyr Ala Gly Pro Val Asn Asn
         95                 100                 105

Pro Glu Phe Thr Ile Pro Gln Gly Glu Tyr Gln Val Leu Leu Glu Leu
        110                 115                 120

Tyr Thr Glu Lys Arg Ser Thr Val Ala Cys Ala Asn Ala Thr Ile Met
125                 130                 135                 140

Cys Ser
```

(2) INFORMATION FOR SEQ ID NO:3:

(i) SEQUENCE CHARACTERISTICS:
        (A) LENGTH: 133 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Trp Pro Thr His Thr Val Cys Lys Glu Glu Asn Leu Glu Ile Tyr Tyr
1               5                   10                  15

Lys Ser Cys Asp Pro Gln Gln Asp Phe Ala Phe Ser Ile Asp Arg Cys
             20                  25                  30

Ser Asp Val Thr Thr His Thr Phe Asp Ile Arg Ala Ala Met Val Leu
         35                  40                  45

Arg Gln Ser Ile Lys Glu Leu Tyr Ala Lys Val Asp Leu Ile Ile Asn
    50                  55                  60

Gly Lys Thr Val Leu Ser Tyr Ser Glu Thr Leu Cys Gly Pro Gly Leu
65                  70                  75                  80

Ser Lys Leu Ile Phe Cys Gly Lys Lys Gly Glu His Leu Tyr Tyr
             85                  90                  95

Glu Gly Pro Ile Thr Leu Gly Ile Lys Glu Ile Pro Gln Gly Asp Tyr
            100                 105                 110

Thr Ile Thr Ala Arg Leu Thr Asn Glu Asp Arg Ala Thr Val Ala Cys
        115                 120                 125

Ala Asp Phe Thr Val
        130
```

(2) INFORMATION FOR SEQ ID NO:4:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

GACTCCATGG GCGGCGGTGG GAAAGCCTG    29

(2) INFORMATION FOR SEQ ID NO:5:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GACTAGATCT GGAGCACATG ATAGTAGCAT                                        30

(2) INFORMATION FOR SEQ ID NO:6:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GACTGGATCC GCCATCATGA AGGGTTTCAC AGCCAC                                 36

(2) INFORMATION FOR SEQ ID NO:7:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

GACTGGTACC AGCAGCTGCA CTCTTTGGG                                         29

(2) INFORMATION FOR SEQ ID NO:8:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

AGCTAAGCTT CCGCCACCAT GAAGGGTTTC ACAGCC                                 36

(2) INFORMATION FOR SEQ ID NO:9:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

CAGTCTCGAG TTAAGCGTAG TCTGGGACGT CGTATGGGTA GGAGCACATG ATAGTAGCAT       60
TG                                                                     62

(2) INFORMATION FOR SEQ ID NO:10:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
GACTGGTACC AGCAGCTGCA CTCTTTGGG                                         29

(2) INFORMATION FOR SEQ ID NO:11:

(i) SEQUENCE CHARACTERISTICS:
        (A) LENGTH: 514 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:11:

NAATTCGCGA GATTTTTCCC AGCTGCAGTG GAGGCGGCGG TGGGAAAGCC TGGCCCACAC        60

ACGTGGTCTG TAGCGACAGG CTTTGGAAGT GCTCTACCAG AGTTGCGATC CATTACAAGA       120

TTTTGGCTTT TCTGTTGAAA AGTGTTCCAA GCAATTAAAA TCAAATATCA ACATTAGATT       180

TGGAATTATT CTGAAGGACA TCAAAGAGCT TTTTCTTGAC CTAGCTCTCA TGTNTCAAGG       240

CTCATCTGTT TTGAATTTCT CCTATCCCAT CTGTGAGGCG GCTCTGCCAA GTTTTCTTTC       300

TGTGGAAGAA GGAAAGGAGA GCAGATTTAC TATGCTNGGG CTGTCAATAA TNCNGAATTT       360

ACTATTTCCT CANGGGGAT TACCAGGTTT TGCTGGGACT GTACAATGAA AAACGGTCCA        420

CCGNGGCNGT GCCATGGTAC TATCGNGTGG TCCGACTGTG GCCNTAGGAA AATCACACCA       480

TTGNATTCGG GGNCNCCAGT CCTTGATNAC CNAN                                   514

(2) INFORMATION FOR SEQ ID NO:12:

(i) SEQUENCE CHARACTERISTICS:
        (A) LENGTH: 457 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:12:

CACAGCCACT CTCTTCCTCT GGACTCTAAT TTTNCCCAGC TGCAGTGGAG GCGGCGGTGG        60

GAAAGCCTGG CCCACACACG TGGTCTGTAG CGACANGGCT TGGAAGTGCT CTACCAGAGT       120

TGCGATCCAT TACAAGATTT TGGCTTTTCT GTTGAAAAGT GTTCCAAGCA ATTAAAATCA       180

AATATCAACA TTAGATTTGG AATTATTCTG AGAGAGGACA TCAAAGAGCT TTTTCTTGAC       240

CTAGCTCTCA TGTCTCAAGG CTCATCTGTT TTNAATTTCT CCTATCCCAT CTGTNAGGCG       300

GCTCTGCCCA GTTTTCTTT CTGTGGAAGA AGGAAAGGAG AGCAGATTTA CTATGCTGGG       360

CCTGTTCAAT AAATCCTGAA TTTAACTATT CCTCAGGGAG AATACCAGGT TTTGCTGGAA       420

CTGTACACTG AAAAACGGTC CACCGTGGCC TGTGCCA                                457

(2) INFORMATION FOR SEQ ID NO:13:

(i) SEQUENCE CHARACTERISTICS:
        (A) LENGTH: 413 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

TTGGTAACNT GTGAGGAAGC ACTCCTAAAA AGTTGAAAAG CAGGTGAGTC TGGTGGGAGG        60

CGACCAATTA GAGAAAAAGG ATGGACCCTC AAGACTGCTT AAGGACTGCC AAGAGGCTCC       120
```

| | |
|---|---|
| TTAGAAACAG ATACATTCGG GGACTTCATT ACATCTGTGG AGTCTGGGGA TGTCTGGTCC | 180 |
| TGGGACTAAA ATTAGCAGCT GCACTCTTTG GGGGCGCTTC TTTGTAGAGC CTCTCTCTGT | 240 |
| CATCAGCTGC TTCTCCTCCC ACAGTAGGTT CAGTCAGAGG AGCTTGGAGG TCCCACGAGA | 300 |
| TGCAGCTGGC TGTGATTTTT GCTACAGGCC ACAGTCAGGA GCACATGATA GTAGCATTGG | 360 |
| CACAGGCCAC GGTGGACCGT TTTTCAGTGT ACAGTTCCAG CAAAACCTGG GTA | 413 |

(2) INFORMATION FOR SEQ ID NO:14:

(i) SEQUENCE CHARACTERISTICS:
        (A) LENGTH: 320 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

| | |
|---|---|
| GGACATCAAA GAGCTTTTTC TTGACCTAGC TCTCATGTCT CAAGGCTCAT CTGTTTTGAA | 60 |
| TTTCTCCTAT CCCATCTGTG AGGCGGCTCT GCCAAGTTTT CTTTCTGTGG AAGAAGGAAA | 120 |
| GGAGAGCAGA TTTACTATGC TGGGCCTGTC AATAATCCTG AATTTACTAT TCCTCAGGGA | 180 |
| GAATACCAGG TTTTGCTGGA ACTGTACACT GAAAAACGGT CCACCGTGGG CCTGTGNCAA | 240 |
| TGCTTACTAT TCATGTGCTC CTGACTGTGG GCCTGTTAGC AAAAANTCAC AGNCAGCTGC | 300 |
| ATCTCGTNGG GAACCTTCCA | 320 |

(2) INFORMATION FOR SEQ ID NO:15:

(i) SEQUENCE CHARACTERISTICS:
        (A) LENGTH: 264 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

| | |
|---|---|
| GGCACGAGCC CACCATGAAG GGTTTCACAG CCACTCTCTT CCTCTGGACT CTCATTTTTC | 60 |
| CCAGCTGCAG TGGAGGCGGC GGTGGGGAAA GCCTGGCCCA CACACGTGGT CTGTAGCGAC | 120 |
| AGNCTTTGGG AAGTGCTCTA CCAGAGTTGC GATCCATTAC AAGATTTTGG CTTTTCTGTT | 180 |
| GAAAAGTGTT CCAAGCAATT AAAATCAAAT ATCAACATTA GATTTGGANT TATTCTGAGA | 240 |
| GAGGACATCA ANGAGCTTTT TTTT | 264 |

(2) INFORMATION FOR SEQ ID NO:16:

(i) SEQUENCE CHARACTERISTICS:
        (A) LENGTH: 249 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

| | |
|---|---|
| GATCGATTAC AAGATNTTGG CTTNTCTGTT GAAAAGTGTT CCAAGCAATT AAAATCAAAT | 60 |
| ATCAACATTA GATTTGGAAT TATTCTGAGA GAGGACATCA AAGAGCTTTT TCTTGACCTA | 120 |
| GCTCTCATGT CTCAAGGCTC ATCTGTTTTG ANTTTCTCCT ATCCCATCTG TGAGGCGGCT | 180 |
| CTGCCNAAGT TTTCTTTCTG TGGNAGAAGG AAANGGGGNC AGNTTACTT NTTCTTGTNC | 240 |

-continued

```
NTTTCNATT                                                                    249
```

(2) INFORMATION FOR SEQ ID NO:17:

(i) SEQUENCE CHARACTERISTICS:
        (A) LENGTH: 60 amino acids
        (B) TYPE: amino acid
        (C) STRANDEDNESS: single
        (D) TOPOLOGY: Not Relevant (ii) MOLECULE TYPE: peptide (xi) SEQUENCE DESCRIPTION: SEQ ID NO:17:

```
Trp Pro Thr His Val Cys Leu Glu Tyr Ser Cys Asp Pro Gln Asp Phe
1               5                   10                  15

Phe Ser Cys Ser Ile Arg Leu Arg Ile Lys Glu Leu Leu Gly Val Leu
            20                  25                  30

Ser Cys Leu Lys Phe Cys Gly Lys Gly Glu Tyr Tyr Gly Pro Ile Pro
            35                  40                  45

Gln Gly Tyr Leu Glu Arg Thr Val Ala Cys Ala Thr
    50                  55                  60
```

HUMAN ONCOGENE INDUCED SECRETED PROTEIN I

CROSS-REFERENCE TO RELATED APPLICATIONS

This application hereby claims priority benefit to U.S. Appl. Ser. No. 60/033,869, filed Dec. 20, 1996 and U.S. Appl. Ser. No. 60/037,388, filed Feb. 7, 1997, which are hereby incorporated by reference.

BACKGROUND OF THE INVENTION

1. Field of the Invention

Isolated nucleic acid molecules are provided encoding a human oncogene induced secreted protein I (HOIPS I). HOIPS I polypeptides are also provided, as are vectors, host cells and recombinant methods for producing the same. Also provided are diagnostic methods for detecting myeloid cells expressing the HOIPS I gene and therapeutic methods for treating cell-proliferative diseases.

2. Related Art

Hematopoiesis is the development and formation of blood cells in the bone marrow, and is critical to the proper functioning of the immune response. Differentiation of the myeloid cell lineage (granulocytes and monocytes/macrophages) termed myelopoiesis commences in the human fetus at approximately six weeks of gestation. In the early stages of myelopoiesis, colony-forming units for granulocytes/monocytes (CFU-GMs) can be induced along either the granulocyte or monocyte pathways. Induction of the CFU-GM's along the granulocyte pathway results in distinct morphological stages of development, ultimately terminating in the characteristic trilobed structure of polymorphonuclear leukocytes, also known as granulocytes.

Induction of CFU-GMs along the monocyte pathway gives rise initially to proliferating monoblasts. Monoblasts differentiate into promonocytes and, ultimately, into mature monocytes. Monocytes are considered to be circulating immature macrophages, which are highly differentiated cells found in various tissues.

Monocyte-macrophages are known to secrete a number of biologically active polypeptides called cytokines that affect the functions of other cells. Interleukin-1 (IL-1), interleukin-6 (IL-6), and tumor necrosis factor-alpha (TNF-α) are all cytokines secreted by monocytes/macrophages that play an important role in hematopoiesis.

A continued need exists for the further identification and characterization of the other cytokines and growth factors involved in hematopoiesis and immunoregulation.

Abnormal expression of the genes encoding the various cytokines and growth factors involved in cell differentiation and proliferation can result in neoplasias, including leukemias. Leukemia is defined as a progressive malignant disease of the blood-forming organs, characterized by distorted proliferation and development of leukocytes and their precursors in the blood and bone marrow. The leukemias account for approximately 3 percent of all cancers in the United States. (Li, F. P., "The Chronic Leukemias: Etiology and Epidemiology," in $Neoplastic\ Diseases\ of\ the\ Blood$, vol. I, pp. 7–17, Wiernik et al. eds. (1985)).

Oncogenes have been implicated as a cause of human leukemias. Gelmann, E. P. et al., "The Etiology of Acute Leukemia: Molecular Genetics and Viral Oncology," in $Neoplastic\ Diseases\ of\ the\ Blood$, vol. I, pp. 161–182, Wiernik et al. eds. (1985). An oncogene is a gene that brings about or contributes to neoplastic transformation of cells by encoding proteins which regulate cell growth and differentiation. Retroviral and cellular oncogenes arise from cellular genes called proto-oncogenes, which appear to play an important role in normal hematopoietic cell growth and differentiation.

The isolation and characterization of viral oncogenes (v-onc) have facilitated the cloning and identification of the cellular oncogenes (c-onc) which derive their names from the respective viral genes. They are highly conserved among species, and homologs are found in all vertebrates, in lower organisms, and in humans. (Gelmann et al.) The role of c-onc genes in neoplasia has been investigated extensively.

The retroviral oncogene v-myb transforms myelomonocytic hematopoietic cells in vivo and in vitro. (Moscovici, C. et al., $Adv.\ Viral\ Oncol.$ 1:83–106 (1982)). The v-myb oncogene was originally defined by two naturally occurring avian retroviruses, AMV and E26, that induce myeloid leukemias in chickens. (Moscovici et al.) The v-myb oncogenes are derived from a normal, cellular proto-oncogene, c-myb, which is expressed in high levels in all immature hematopoietic lineages. (Klempnauer, K. H. et al., $Cell$ 31:537–547 (1984)). In contrast, v-myb oncogenes only transform a few cell types, such as the immature myeloid precursors of neutrophils and macrophages. Both c-myb and v-myb encode nuclear, DNA binding proteins (i.e. transcription activators) that regulate the phenotypes of normal and transformed hematopoietic cells respectively. (Ness, S. A. et al., $Cell$ 59: 1115–1125 (1989); Burk, 0. and Klempnauer, K. H., $EMBO\ J.$ 10(12):3713–3719 (1991)). The transforming activity of these proteins is regulated by cell type-specific cofactors. The DNA-binding domain of the v-myb proteins corresponds to the domain of several other myb-related DNA-binding proteins isolated from such diverse species as mammals, insects, and plants. (Queva et al. 1992)

An interesting feature of the v-myb oncogene is that it not only blocks differentiation, but it also dictates the differentiation phenotype of the myeloid cells that it transforms. (Ness, S. A. et al., $Cell$ 59:1115–1125 (1989)). Expression of v-myb in myeloid cells results in them acquiring an immature phenotype. (Burk and Klempnauer, 1991). In addition, it has been shown that minor changes in the structure of the v-Myb protein determine whether the transformed cells take on the phenotype of immature macrophages or immature granulocytes, (Golay, J. et al., $Cell$ 55:1147–1158 (1988)). Moreover, temperature-sensitive v-myb transformed cells induced to differentiate can be induced to retrodifferentiate. (Introna, M. et al., $Cell$ 63:1287–1297 (1990)). Different forms of v-myb impose alternate phenotypes of differentiation on transformed myeloid cells by regulating unique sets of differentiation specific genes. (Introna, M. et al., $Cell$ 63:1287–1297 (1990)).

Two genes, identified as mim-1 and MD-1, are known to be regulated by v-myb. (Ness et al., 1989; Burk and Klempnauer, 1991). The mim-1 gene is specifically expressed in normal, immature, granulocytes and encodes a 35kD secretable protein that is stored in the granules of those cells. (Ness et al., 1989; Queva, C. et al., $Development$ 114:125–133 (1992)). Indeed, mim-1 encodes one of the most abundant proteins found in granulocytes, and the high level of expression suggests that it may be a structural component of the promyelocyte granule. (Ness et al. 1989). When promyelocytes undergo terminal differentiation to neutrophil granulocytes, a decrease in the level of mim-1 protein is observed. (Queva et al.) Moreover, analysis of chick embryo development shows that mim-1 MRNA transcripts are found where granulopoiesis occurs. (Queva et al.) Thus, mim-1 is the first described marker for cells that are differentiating into the granulocytic lineage. (Queva et al.; Introna et al.).

The mim-1 gene is one of a number v-myb-regulated genes that contribute to the unique differentiation phenotype displayed by both normal and transformed myeloid cells. Those genes, which include MD-1, must by definition be regulated similarly to mim-1 by the various forms of the v-myb protein. (Ness et al.) It is likely that a number of different structural changes to the myb protein will alter the phenotype of myeloid cells transformed by the v-myb oncogene and affect its capacity to regulate its target genes, including mim-1 and MD-1. (Introna et al.)

Thus, v-myb acts as a master gene in hematopoietic cell differentiation by regulating the expression of a unique set of genes within the myelomonocytic lineage. (Introna et al.) Because these genes are expected to be important regulators of cell differentiation and proliferation, their identification is critical to understanding the molecular mechanisms of neoplasia, transformation, and growth control. Thus, a need exists in the art for the identification of other genes involved in hematopoietic cell differentiation.

SUMMARY OF THE INVENTION

The present invention provides isolated nucleic acid molecules comprising a polynucleotide encoding the HOIPS I polypeptide having the amino acid sequence shown in FIGS. 1A–1B (SEQ ID NO:2) or the amino acid sequence encoded by the cDNA clone deposited with the American Type Culture Collection ("ATCC"), Patent Depository, 10801 University Boulevard, Manassas, Va. 20110-2209, on Dec. 16, 1996. (ATCC Deposit Number 97825).

The present invention also relates to recombinant vectors, which include the isolated nucleic acid molecules of the present invention, and to host cells containing the recombinant vectors, as well as to methods of making such vectors and host cells and for using them for production of HOIPS I polypeptides or peptides by recombinant techniques.

The invention further provides an isolated HOIPS I polypeptide having an amino acid sequence encoded by a polynucleotide described herein.

In another embodiment, the present invention provides a method for inhibiting abnormal cell proliferation or differentiation by administering to the abnormally proliferating or differentiating cell, a synthetic DNA or RNA construct of the present invention, wherein said synthetic DNA or RNA construct represses the functional expression of the HOIPS I gene. In an especially preferred embodiment, said DNA construct is operably linked to an inducible promoter.

In another embodiment, the present invention provides a method for identifying individuals who are believed to be predisposed to cell proliferative or differentiation disorders comprising the step of identifying individuals who have only one active allele of the HOIPS I gene.

The present invention provides a diagnostic method useful during diagnosis of a cell proliferative or cell differentiation disorder.

An additional aspect of the invention is related to a method for treating an individual in need of an increased level of HOIPS I activity in the body comprising administering to such an individual a composition comprising a therapeutically effective amount of an isolated HOIPS I polypeptide of the invention or an agonist thereof.

A still further aspect of the invention is related to a method for treating an individual in need of a decreased level of HOIPS I activity in the body comprising, administering to such an individual a composition comprising a therapeutically effective amount of an HOIPS I antagonist.

BRIEF DESCRIPTION OF THE FIGURES

FIGS. 1A–1B show the nucleotide (SEQ ID NO:1) and deduced amino acid (SEQ ID NO:2) sequences of HOIPS I. The protein has a leader sequence of about 20 amino acid residues and a deduced molecular weight of about 17.8 kDa. The predicted amino acid sequence of the mature HOIPS I protein is also shown in FIGS. 1A–1B (SEQ ID NO:2).

FIG. 2 shows the regions of similarity between the amino acid sequences of the HOIPS I protein and chicken MD-1 (SEQ ID NO:3). The consensus sequence is shown (SEQ ID NO: 17).

DETAILED DESCRIPTION

Figure 3:
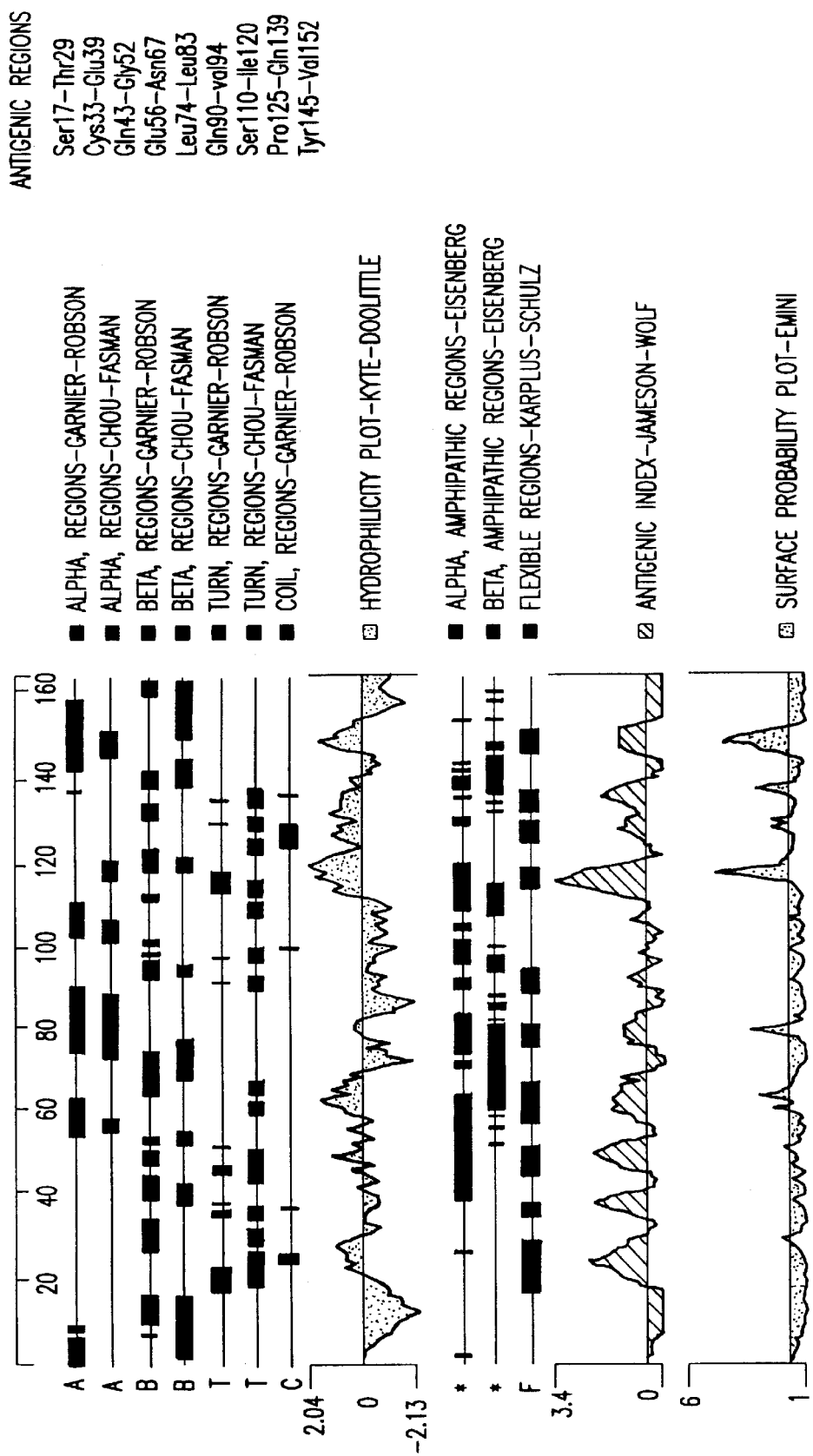
FIG. 3 shows an analysis of the HOIPS I amino acid sequence. Alpha, beta, turn and coil regions; hydrophilicity and hydrophobicity; amphipathic regions; flexible regions; antigenic index and surface probability are shown. In the "Antigenic Index—Jameson-Wolf" graph, amino acid residues about 17 to about 29, about 33 to about 39, about 43 to about 52, about 56 to about 67, about 74 to about 83, about 90 to about 94, about 110 to about 120, about 125 to about 139, and about 145 to about 152 in FIGS. 1A–1B correspond to the shown highly antigenic regions of the HOIPS I protein. These highly antigenic fragments in FIGS. 1A–1B correspond to the following fragments, respectively in SEQ ID NO:2: amino acid residues about −4 to about 9, about 13 to about 19, about 23 to about 32, about 36 to about 47, about 54 to about 63, about 70 to about 74, about 90 to about 100, about 105 to about 119, and about 125 to about 132.

The present invention provides isolated nucleic acid molecules comprising a polynucleotide encoding a HOIPS I polypeptide having the amino acid sequence shown in FIGS. 1A–1B (SEQ ID NO:2), which was determined by sequencing a cloned cDNA. The HOIPS I protein of the present invention shares sequence homology with the chicken MD-1 protein. (FIG. 2) (SEQ ID NO:3). The nucleotide sequence shown in FIGS. 1A–1B (SEQ ID NO:1) was obtained by sequencing the HTOCD71X clone, which was deposited on Dec. 16, 1996 at the American Type Culture Collection, 12301 Park Lawn Drive, Rockville, Md. 20852. (ATCC accession number 97825) The deposited clone is contained in the pBluescript SK(-) plasmid (Stratagene, LaJolla, Calif.).

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–1B, a nucleic acid molecule of the present invention encoding a HOIPS I polypeptide may be obtained using standard cloning and screening procedures, such as those for cloning cDNAs using mRNA as starting material. Illustrative of the invention, the nucleic acid molecule described in FIGS. 1A–1B (SEQ ID NO:1) was discovered in a cDNA library derived from human tonsils tissue. The gene was also identified in cDNA libraries from the following tissues: bone marrow, dendritic cells, fetal and adult brain macrophages, B cells, and lymph nodes. The determined nucleotide sequence of the HOIPS I cDNA of FIGS. 1A–1B (SEQ ID NO:1) contains an open reading frame encoding a protein of 162 amino acid residues and a deduced molecular weight of about 17.8 kDa. The HOIPS I protein shown in FIGS. 1A–1B (SEQ ID NO:2) is about 45% identical to, and about 64% similar to, the chicken MD-1 protein (FIG. 2) in a 132 amino acid residue overlap.

The present invention also provides the mature form(s) of the HOIPS I protein of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature HOIPS I polypeptides having the amino acid sequence encoded by the cDNA clone contained in the host deposited with the ATCC on Dec. 16, 1996, (ATCC Deposit No. 97825) and as shown in FIGS. 1A–1B (SEQ ID NO:2). By the mature HOIPS I protein having the amino acid sequence encoded by the cDNA clone contained in the host deposited with the ATCC on Dec. 16, 1996, (ATCC Deposit No. 97825) is meant the mature form(s) of the HOIPS I protein produced by expression in a mammalian cell (e.g., COS cells, as described below) of the complete open reading frame encoded by the human DNA sequence of the clone contained in the vector in the deposited host. As indicated below, the mature HOIPS I having the amino acid sequence encoded by the cDNA clone contained in the host deposited with the ATCC on Dec. 16, 1996, (ATCC Deposit No. 97825) may or may not differ from the predicted "mature" HOIPS I protein shown in FIGS. 1A–1B (amino acids from about 1 to about 142 in SEQ ID NO:2) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271–286 (1985)) and von Heinje (*Nucleic Acids Res.* 14:4683–4690 (1986)) can be used. The accuracy of predicting the cleavage points of known mammalian secretory proteins for each of these methods is in the range of 75–80%. von Heinje, supra. However, the two methods do not always produce the same predicted cleavage point(s) for a given protein.

In the present case, the predicted amino acid sequence of the complete HOIPS I polypeptides of the present invention were analyzed by a computer program ("PSORT") (K. Nakai and M. Kanehisa, *Genomics* 14:897–911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage sites between amino acids 20 and 21 in FIGS. 1A–1B (SEQ ID NO:2). Thereafter, the complete amino acid sequences were further analyzed by visual inspection, applying a simple form of the (-1, -3) rule of von Heinje. von Heinje, supra. Thus, the leader sequence for the HOIPS I protein is predicted to consist of amino acid residues -20 to -1 in SEQ ID NO:2. However, while the predicted mature HOIPS I protein consists of residues 1–142, the present inventors have identified other possible cleavage sites resulting in mature proteins having the following amino acid residues shown in SEQ ID NO:2: -7–142, -6–142, -5–142, -4–142, -3–142, -2–42, -1–142, 2–142, 3–142, 4–142, 5–142, 6–142, 7–142, 8–142, 9–142, 10–142, 11–142, 12–142, 13–142, 14–142.

As one of ordinary skill would appreciate, due to the possibilities of sequencing errors discussed above, as well as the variability of cleavage sites for leaders in different known proteins, the predicted HOIPS I polypeptide encoded by the deposited cDNA comprises about 162 amino acids, but may be anywhere in the range of 142–182 amino acids; and the predicted leader sequence of this protein is about 20 amino acids, but may be anywhere in the range of about 13 to about 33 amino acids.

As indicated, nucleic acid molecules of the present invention may be in the form of RNA, such as MRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) shown in FIGS. 1A–1B (SEQ ID NO:1); DNA molecules comprising the coding sequence for the mature HOIPS I protein shown in FIGS. 1A–1B (last 142 amino acids) (SEQ ID NO:2); and DNA molecules which comprise a sequence substantially different from those described above but which, due to the degeneracy of the genetic code, still encode the HOIPS I protein. Of course, the genetic code is well known in the art. Thus, it would be routine for one skilled in the art to generate such degenerate variants.

In another aspect, the invention provides isolated nucleic acid molecules encoding the HOIPS I polypeptide having an amino acid sequence as encoded by the cDNA clone contained in the plasmid deposited with the ATCC on Dec. 16, 1996 (ATCC Deposit No. 97825). In a further embodiment, nucleic acid molecules are provided encoding the mature HOIPS I polypeptide or the full-length polypeptide lacking the N-terminal methionine. The invention also provides an isolated nucleic acid molecule having the nucleotide sequence shown in FIGS. 1A–1B (SEQ ID NO:1) or the nucleotide sequence of the HOIPS I cDNA contained in the above-described deposited clone, or a nucleic acid molecule having a sequence complementary to one of the above sequences. Such isolated molecules, particularly DNA molecules, are useful as probes for gene mapping, by in situ hybridization with chromosomes, and for detecting expression of the HOIPS I gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA or the nucleotide sequence shown in FIGS. 1A–1B (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50, 100, 150, 200, 250, 300, 350, 400, 450, or 500 nt in length are also useful according to the present invention as are fragments corresponding to most, if not all, of the nucleotide sequence of the deposited cDNA or as shown in FIGS. 1A–1B (SEQ ID NO:1). By a fragment at least 20 nt in length, for example, is intended fragments which include 20 or more contiguous bases from the nucleotide sequence of the deposited cDNA or the nucleotide sequence as shown in FIGS. 1A–1B (SEQ ID NO: 1).

Preferred nucleic acid fragments of the present invention include nucleic acid molecules encoding epitope-bearing portions of the HOIPS I protein. In particular, such nucleic acid fragments of the present invention include nucleic acid molecules encoding: a polypeptide comprising amino acid residues from about −4 to about 9 of SEQ ID NO:2, a polypeptide comprising amino acid residues from about 13 to about 19 of SEQ ID NO:2, a polypeptide comprising amino acid residues from about 23 to about 32 of SEQ ID NO:2, a polypeptide comprising amino acid residues from about 36 to about 47 of SEQ ID NO:2, a polypeptide comprising amino acid residues from about 54 to about 63 of SEQ ID NO:2, a polypeptide comprising amino acid residues from about 70 to about 74 of SEQ ID NO:2, a polypeptide comprising amino acid residues from about 90 to about 100 of SEQ ID NO:2, a polypeptide comprising amino acid residues from about 105 to about 119 of SEQ ID NO:2, and a polypeptide comprising amino acid residues from about 125 to about 132 of SEQ ID NO:2. The inventors have determined that the above polypeptide fragments are antigenic regions of the HOIPS I protein. Methods for determining other such epitope-bearing portions of the HOIPS I protein are described in detail below.

In addition, the present inventors have identified the following cDNA clone related to extensive portions of SEQ ID NO: 1: HCASG14R (SEQ ID NO: 11).

The following public ESTs, which relate to portions of SEQ ID NO:1, have also been identified: GenBank Accession No. AA340310 (SEQ ID NO:12); GenBank Accession No. T91708 (SEQ ID NO:13); GenBank Accession No. T92475 (SEQ ID NO:14); GenBank Accession No. T84854 (SEQ ID NO:15); and GenBank Accession No. C02431 (SEQ ID NO:16).

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone deposited with the ATCC on Dec. 16, 1996 (ATCC Deposit No. 97825). By "stringent hybridization conditions" is intended overnight incubation at 42° C. in a solution comprising: 50% formamide, 5×SSC (750 mM NaCl, 75mM trisodium citrate), 50 mM sodium phosphate (pH 7.6), 5×Denhardt's solution, 10% dextran sulfate, and 20 u/ml denatured, sheared salmon sperm DNA, followed by washing the filters in 0×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIGS. 1A–1B (SEQ ID NO:1)). Of course, a polynucleotide which hybridizes only to a poly A sequence (such as the 3' terminal poly(A) tract of the HOIPS I cDNA shown in FIGS. 1A–1B (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a HOIPS I polypeptide may include, but are not limited to those encoding the amino acid sequence of the mature polypeptide, by itself; the coding sequence for the mature polypeptide and additional sequences, such as those encoding the about 20 amino acid leader or secretory sequence, such as a pre-, or pro- or prepro- protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the HOIPS I fused to Fc at the N- or C-terminus.

The present invention further relates to variants of the nucleic acid molecules of the present invention, which encode portions, analogs or derivatives of the HOIPS I protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the HOIPS I protein or portions thereof. Also especially preferred in this regard are conservative substitutions.

Further embodiments of the invention include isolated nucleic acid molecules comprising a polynucleotide having a nucleotide sequence at least 95% identical, and more preferably at least 96%, 97%, 98% or 99% identical to (a) a nucleotide sequence encoding the polypeptide having the amino acid sequence in SEQ ID NO:2; (b) a nucleotide sequence encoding the polypeptide having the amino acid sequence in SEQ ID NO: 2, but lacking the N-terminal methionine; (c) a nucleotide sequence encoding the polypeptide having the amino acid sequence at positions from about 1 to about 142 in FIGS. 1A–1B SEQ ID NO:2; (d) a nucleotide sequence encoding the polypeptide having the amino acid sequence encoded by the cDNA clone contained in ATCC Deposit No. 97825; (e) a nucleotide sequence encoding the mature HOIPS I polypeptide having the amino acid sequence encoded by the cDNA clone contained in ATCC Deposit No. 97825; or (f) a nucleotide sequence complementary to any of the nucleotide sequences in (a), (b), (c), (d), or (e).

By a polynucleotide having a nucleotide sequence at least, for example, 95% "identical" to a reference nucleotide sequence encoding a HOIPS I polypeptide is intended that the nucleotide sequence of the polynucleotide is identical to the reference sequence except that the polynucleotide sequence may include up to five point mutations per each 100 nucleotides of the reference nucleotide sequence encoding the HOIPS I polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to, for instance, the nucleotide sequence shown in SEQ ID NO:1 or to the nucleotide sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. Bestfit uses the local homology algorithm of Smith and Waterman, *Advances in Applied Mathematics* 2: 482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 95%, 96%, 97%, 98% or 99% identical to the nucleic acid sequence shown in SEQ ID NO:1 or to the nucleic acid sequence of the deposited cDNA, irrespective of whether they encode a polypeptide having HOIPS I activity. This is because even where a particular nucleic acid molecule does not encode a polypeptide having HOIPS I activity, one of skill in the art would still know how to use the nucleic acid molecule, for instance, as a hybridization probe or as a polymerase chain reaction (PCR) primer. Uses of the nucleic acid molecules of the present invention that do not encode a polypeptide having HOIPS I activity include, inter alia, (1) isolating the HOIPS I gene or allelic variants thereof in a cDNA library; (2) in situ hybridization (e.g., "FISH") to metaphase chromosomal spreads to provide precise chromosomal location of the HOIPS I gene, as described in Verma et al., *Human Chromosomes: A Manual of Basic Techniques*, Pergamon Press, New York (1988); and Northern Blot analysis for detecting HOIPS I MRNA expression in specific tissues.

Preferred, however, are nucleic acid molecules having sequences at least 95%, 96%, 97%, 98% or 99% identical to the nucleic acid sequence shown in SEQ ID NO:1 or to the nucleic acid sequence of the deposited cDNA which do, in fact, encode a polypeptide having HOIPS I protein activity. By "a polypeptide having HOIPS I activity" is intended polypeptides exhibiting activity similar, but not necessarily identical, to an activity of the HOIPS I protein of the invention (either the full-length protein or, preferably, the mature protein).

Of course, due to the degeneracy of the genetic code, one of ordinary skill in the art will immediately recognize that a large number of the nucleic acid molecules having a sequence at least 95%, 96%, 97%, 98%, or 99% identical to the nucleic acid sequence of the deposited cDNA or the nucleic acid sequence shown in SEQ ID NO:1 will encode a polypeptide "having HOIPS I protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having HOIPS I protein activity. This is because the skilled artisan is fully aware of amino acid substitutions that are either less likely or not likely to significantly effect protein function (e.g., replacing one aliphatic amino acid with a second aliphatic amino acid).

For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that proteins are surprisingly tolerant of amino acid substitutions.

Vectors and Host Cells

The present invention also relates to vectors which include the isolated DNA molecules of the present invention, host cells which are genetically engineered with the recombinant vectors, and the production of HOIPS I polypeptides or fragments thereof by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coil* lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coil* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS and Bowes melanoma cells; and plant cells. Appropriate culture mediums and conditions for the above-described host cells are known in the art.

Among vectors preferred for use in bacteria include pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, PMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as antigen for immunizations. In drug discovery, for example, human proteins, such as hIL-5 have been fused with Fc portions for the purpose of high-throughput screening assays to identify antagonists of hIL-5. See, D. Bennett et al., *Journal of Molecular Recognition*, Vol. 8 52–58 (1995) and K. Johanson et al., *The Journal of Biological Chemistry*, Vol. 270, No. 16, pp 9459–9471 (1995).

The HOIPS I protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

HOIPS I Polypeptides and Fragments

The invention further provides an isolated HOIPS I polypeptide having the amino acid sequence encoded by the deposited cDNA, or the amino acid sequence in FIGS. 1A–1B (SEQ ID NO:2), or a peptide or polypeptide comprising a portion of the above polypeptides.

It will be recognized in the art that some amino acid sequences of the HOIPS I polypeptide can be varied without significant effect of the structure or function of the protein. If such differences in sequence are contemplated, it should be remembered that there will be critical areas on the protein which determine activity.

Thus, the invention further includes variations of the HOIPS I polypeptide which show substantial HOIPS I polypeptide activity or which include regions of HOIPS I protein such as the protein portions discussed below. Such mutants include deletions, insertions, inversions, repeats, and type substitutions. As indicated above, guidance concerning which amino acid changes are likely to be phenotypically silent can be found in Bowie, J.U., et al., "Deciphering the Message in Protein Sequences: Tolerance to Amino Acid Substitutions," *Science* 247:1306–1310 (1990).

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the HOIPS I protein. The prevention of aggregation is highly desirable. Aggregation of proteins not only results in a loss of activity but can also be problematic when preparing pharmaceutical formulations, because they can be immunogenic. (Pinckard et al., *Clin Exp. Immunol.* 2:331–340 (1967); Robbins et al., *Diabetes* 36:838–845 (1987); Cleland et al. *Crit. Rev. Therapeutic Drug Carrier Systems* 10:307–377 (1993)).

As indicated, changes are preferably of a minor nature, such as conservative amino acid substitutions that do not significantly affect the folding or activity of the protein (see Table 1).

TABLE 1

Conservative Amino Acid Substitutions.

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Of course, the number of amino acid substitutions a skilled artisan would make depends on many factors, including those described above. Generally speaking, the number of amino acid substitutions for any given HOIPS I polypeptide will not be more than 50, 40, 30, 20, 10, 5, or 3.

Amino acids in the HOIPS I protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as in vitro proliferative activity.

The polypeptides of the present invention are preferably provided in an isolated form. By "isolated polypeptide" is intended a polypeptide removed from its native environment. Thus, a polypeptide produced and/or contained within a recombinant host cell is considered "isolated" for purposes of the present invention. Also intended as an "isolated polypeptide" are polypeptides that have been purified, partially or substantially, from a recombinant host cell or from a native source. For example, a recombinantly produced version of the HOIPS I polypeptide can be substantially purified by the one-step method described in Smith and Johnson, *Gene* 67:31–40 (1988).

The polypeptides of the present invention include the polypeptide encoded by the deposited cDNA including the leader, the mature polypeptide encoded by the deposited cDNA minus the leader (i.e., the mature protein), a polypeptide comprising amino acids about −20 to about 142 in SEQ ID NO:2; a polypeptide comprising the amino acids about −19 to about 142 in SEQ ID NO:2; a polypeptide comprising amino acids about 1 to about 142 in SEQ ID NO:2; as well as polypeptides which are at least 95% identical, more preferably at least 96%, 97%, 98% or 99% identical to those described above and also include portions of such polypeptides with at least 30 amino acids and more preferably at least 50 amino acids.

By a polypeptide having an amino acid sequence at least, for example, 95% "identical" to a reference amino acid sequence of a HOIPS I polypeptide is intended that the amino acid sequence of the polypeptide is identical to the reference sequence except that the polypeptide sequence may include up to five amino acid alterations per each 100 amino acids of the reference amino acid of the HOIPS I polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to, for instance, the amino acid sequence shown in SEQ ID NO:2 or to the amino acid sequence encoded by the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711. When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptides of the present invention are useful as a molecular weight marker on SDS-PAGE gels or on molecular sieve gel filtration columns using methods well known to those of skill in the art.

In another aspect, the invention provides a peptide or polypeptide comprising an epitope-bearing portion of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) Antibodies that react with predetermined sites on proteins. *Science* 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767–778 (1984) at 777.

Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate HOIPS I-specific antibodies include: a polypeptide comprising amino acid residues from about −4 to about 9 of SEQ ID NO:2, a polypeptide comprising amino acid residues from about 13 to about 19 of SEQ ID NO:2, a polypeptide comprising amino acid residues from about 23 to about 32 of SEQ ID NO:2, a polypeptide comprising amino acid residues from about 36 to about 47 of SEQ ID NO:2, a polypeptide comprising amino acid residues from about 54 to about 63 of SEQ ID NO:2, a polypeptide comprising amino acid residues from about 70 to about 74 of SEQ ID NO:2, a polypeptide comprising amino acid residues from about 90 to about 100 of SEQ ID NO:2, a polypeptide comprising amino acid residues from about 105 to about 119 of SEQ ID NO:2, and a polypeptide comprising amino acid residues from about 125 to about 132 of SEQ ID NO:2. As indicated above, the inventors have determined that the above polypeptide fragments are antigenic regions of the HOIPS I protein.

The epitope-bearing peptides and polypeptides of the invention may be produced by any conventional means. (Houghten, R. A., "General method for the rapid solid-phase synthesis of large numbers of peptides: specificity of antigen-antibody interaction at the level of individual amino acids," *Proc. Natl. Acad. Sci. USA* 82:5131–5135 (1985)). This "Simultaneous Multiple Peptide Synthesis (SMPS)" process is further described in U.S. Pat. No. 4,631,211 to Houghten et al. (1986).

As one of skill in the art will appreciate, HOIPS I polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84–86 (1988)). Fusion proteins that have a disulfide-linked dimeric structure due to the IgG part can also be more efficient in binding and neutralizing other molecules than the monomeric HOIPS I protein or protein fragment alone (Fountoulakis et al., *J Biochem* 270:3958–3964 (1995)).

Cancer Diagnosis and Prognosis

It is believed that certain tissues in mammals with cancer, in particular acute myelogenous leukemias, express significantly altered levels of the HOIPS I protein and mRNA encoding the HOIPS I protein when compared to a corresponding "standard" mammal, i.e., a mammal of the same species not having the cancer. Further, it is believed that enhanced levels of the HOIPS I protein can be detected in certain body fluids (e.g., sera, plasma, urine and spinal fluid) from mammals with certain leukemias, e.g. acute myelogenous leukemia, when compared to sera from mammals of the same species not having the leukemia. Thus, the invention provides a diagnostic method useful during myeloma diagnosis, which involves assaying the expression level of the gene encoding the HOIPS I protein in mammalian cells or body fluid and comparing the gene expression level with a standard HOIPS I gene expression level, whereby an increase in the gene expression level over the standard is indicative of certain tumors.

Where a tumor diagnosis has already been made according to conventional methods, the present invention is useful as a prognostic indicator, whereby patients exhibiting enhanced HOIPS I gene expression will be predicted to experience a worse clinical outcome relative to patients expressing the gene at a lower level.

By "assaying the expression level of the gene encoding the HOIPS I protein" is intended qualitatively or quantitatively measuring or estimating the level of the HOIPS I protein or the level of the MRNA encoding the HOIPS I protein in a first biological sample either directly (e.g., by determining or estimating absolute protein level or mRNA level) or relatively (e.g., by comparing to the HOIPS I protein level or MRNA level in a second biological sample).

Preferably, the HOIPS I protein level or mRNA level in the first biological sample is measured or estimated and compared to a standard HOIPS I protein level or mRNA level, the standard being taken from a second biological sample obtained from an individual not having the cancer. As will be appreciated in the art, once a standard HOIPS I protein level or mRNA level is known, it can be used repeatedly as a standard for comparison.

By "biological sample" is intended any biological sample obtained from an individual, cell line, tissue culture, or other source which contains HOIPS I protein or MRNA. Biological samples include mammalian body fluids (such as sera, plasma, urine, synovial fluid and spinal fluid) which contain secreted mature HOIPS I protein, and hematopoietic tissues including the spleen, tonsils, bone marrow, dendritic cells, fetal and adult brain macrophages, B cells, lymph nodes etc.

The present invention is useful for detecting cancer in mammals. In particular the invention is useful during diagnosis of the following pathological cell proliferative neoplasias: acute myelogenous leukemias including acute monocytic leukemia, acute myeloblastic leukemia, acute promyelocytic leukemia, acute myelomonocytic leukemia, acute erythroleukemia, acute megakaryocytic leukemia, and acute undifferentiated leukemia, etc.; and chronic myelogenous leukemias including chronic myelomonocytic leukemia, chronic granulocytic leukemia, etc. Preferred mammals include monkeys, apes, cats, dogs, cows, pigs, horses, rabbits and humans. Particularly preferred are humans.

Total cellular RNA can be isolated from a biological sample using the single-step guanidinium-thiocyanate-phenol-chloroform method described in Chomczynski and Sacchi, *Anal. Biochem.* 162:156–159 (1987). Levels of mRNA encoding the HOIPS I protein are then assayed using any appropriate method. These include Northern blot analysis (Harada et al., *Cell* 63:303–312 (1990)), S1 nuclease mapping (Fujita et al., *Cell* 49:357–367 (1987)), the polymerase chain reaction (PCR), reverse transcription in combination with the polymerase chain reaction (RT-PCR) (Makino et al., *Technique* 2:295–301 (1990)), and reverse transcription in combination with the ligase chain reaction (RT-LCR).

Assaying HOIPS I protein levels in a biological sample can occur using antibody-based techniques. For example, HOIPS I protein expression in tissues can be studied with classical immunohistological methods (Jalkanen, M., et al., *J Cell. Biol.* 101:976–985 (1985); Jalkanen, M., et al., *J Cell. Biol.* 105:3087–3096 (1987)).

Other antibody-based methods useful for detecting HOIPS I protein gene expression include immunoassays, such as the enzyme linked immunosorbent assay (ELISA) and the radioimmunoassay (RIA). Suitable labels are known in the art and include enzyme labels, such as, Glucose oxidase, and radioisotopes, such as iodine ($^{125}I$, $^{121}I$), carbon ($^{14}C$), salphee ($^{35}S$), tritium ($^{3}H$), indium ($^{112}In$), and technetium ($^{99m}Tc$), and fluorescent labels, such as fluorescein and rhodamine, and biotin.

Therapeutics

Pathological cell proliferative disorders are often associated with inappropriate activation of proto-oncogenes. (Gelmann, E. P. et al., "The Etiology of Acute Leukemia: Molecular Genetics and Viral Oncology," in *Neoplastic Diseases of the Blood*, Vol 1., Wiernik, P. H. et al. eds., 161–182 (1985)). Neoplasias are now believed to result from the qualitative alteration of a normal cellular gene product, or from the quantitative modification of gene expression by insertion into the chromosome of a viral sequence, by chromosomal translocation of a gene to a more actively transcribed region, or by some other mechanism. (Gelmann et al.) It is likely that mutated or altered expression of specific genes is involved in the pathogenesis of some leukemias. (Gelmann et al.) Indeed, the human counterparts of the oncogenes involved in some animal neoplasias have been amplified or translocated in some cases of human leukemia and carcinoma. (Gelmann et al.)

For example, c-myc expression is highly amplified in the non-lymphocytic leukemia cell line HL-60. When HL-60 cells are chemically induced to stop proliferation, the level of c-myc is found to be downregulated. (WO 91/15580) However, it has been shown that exposure of HL-60 cells to a DNA construct that is complementary to the 5' end of c-myc or c-myb blocks translation of the corresponding mRNAs which downregulates expression of the c-myc or c-myb proteins and causes arrest of cell proliferation and differentiation of the treated cells. (WO 91/15580; Wickstrom et al., *Proc. Natl. Acad. Sci.* 85:1028 (1988); Anfossi et al., *Proc. Natl. Acad. Sci.* 86:3379 (1989)).

Accordingly, the present invention is directed to the utilization of the HOIPS I gene and its product in gene therapy techniques to treat cell proliferative diseases in individuals. The term "gene therapy" is meant to include the insertion of part of all of the HOIPS I gene, a HOIPS I DNA or RNA construct or HOIPS I gene product into a cell, group of cells, tissue, pathological lesion, organ or organism for the purpose of modulating gene expression, and/or function of the gene product.

Thus, in one embodiment, the present invention provides a method for treating cell proliferative diseases, and in particular acute and chronic myelogenous leukemias, by inserting into an abnormally proliferating cell which expresses the HOIPS I gene a synthetic DNA or RNA construct of the present invention, wherein said DNA or RNA construct represses said expression.

Another embodiment of the present invention provides a method of treating cell-proliferative disorders in individuals comprising administration of one or more active gene copies of the HOIPS I gene to an abnormally proliferating cell or cells. In a preferred embodiment, the HOIPS I gene is a DNA construct comprising a recombinant expression vector effective in expressing a DNA sequence encoding said HOIPS I gene. In another preferred embodiment of the present invention, the DNA construct encoding the HOIPS I gene is inserted into cells to be treated utilizing a retrovirus vector. In a most preferred embodiment, the retroviral vector is defective and will not transform non-proliferating cells.

By "repressing expression of the HOIPS I gene" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

In an especially preferred embodiment, suppression of HOIPS I gene expression in a cell is achieved by administering antisense RNA. Antisense RNAs are RNAs that are complimentary to all or part of the MRNA of the HOIPS I gene. In general, overproduction of antisense RNA has been shown to prevent translation of a given target RNA, thereby blocking the expression of the target gene product. (WO 91/15580). Accordingly, in order to block HOIPS I induced proliferation or differentiation of a cell, antisense RNAs can be introduced into the proliferating or differentiating cells.

The use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoRI site on the 5' end and a HindIII site on the 3' end. Next, the pair of oligonucleotides is heated at 90° C. for one minute and then annealed in 2×ligation buffer (20 mM TRIS HCl pH 7.5, 10 mM $MgCl_2$, 10MM dithiothreitol (DTT) and 0.2 mM ATP) and then ligated to the EcoR1/Hind III site of the retroviral vector PMV7. (WO 91/15580)

It will be appreciated that conditions caused by a decrease in the standard or normal level of HOIPS I activity in an individual, can be treated by administration of HOIPS I protein. Thus, the invention further provides a method of treating an individual in need of an increased level of HOIPS I activity comprising administering to such an individual a pharmaceutical composition comprising an effective amount of an isolated HOIPS I polypeptide of the invention, particularly a mature form of the HOIPS I, effective to increase the HOIPS I activity level in such an individual.

As a general proposition, the total pharmaceutically effective amount of HOIPS I polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the HOIPS I polypeptide is typically administered at a dose rate of about 1 µg/kg/hour to about 50 µg/kg/hour, either by 1–4 injections per day or by continuous subcutaneous infusions, for example, using a mini-pump. An intravenous bag solution may also be employed.

Pharmaceutical compositions containing the HOIPS I of the invention may be administered orally, rectally, parenterally, intracisternally, intravaginally, intra peritoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

For local administration to abnormally proliferating cells, the HOIPS I DNA or RNA constructs or genes may be administered by any method known to those of skill in the art including, but not limited to transfection, electroporation, microinjection of cells, or in vehicles such as liposomes, lipofectin, or as naked DNA or RNA. The DNA of the present invention may be delivered by known gene delivery systems such as, but not limited to, retroviral vectors (Gilboa, *J Virology* 44:845 (1982); Hocke, *Nature* 320:275 (1986); Wilson, et al., *Proc. Natl. Acad. Sci. USA*. 85:3014), vaccinia virus system (Chakrabarty et al., *Mol. Cell Biol.* 5:3403 (1985) or other efficient DNA delivery systems (Yates et al., *Nature* 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for the HOIPS I gene and DNA constructs of the present invention will target said gene and constructs to abnormally proliferating cells and will spare the non-dividing normal cells.

Administration of the HOIPS I gene, DNA or RNA constructs, or gene product useful in the methods of the present invention may be by topical, parenteral, oral, intranasal, intravenous, intramuscular, subcutaneous, or any other suitable means.

The DNA constructs of the present invention may be delivered directly to cell proliferative disorder/disease sites in internal organs, body cavities and the like by use of imaging devices used to guide an injecting needle directly to the disease site. The DNA constructs of the present invention may also be administered to disease sites at the time of surgical intervention.

The DNA dosage administered is dependent upon the age, clinical stage and extent of the disease or genetic predisposition of the individual, location, weight, kind of concurrent treatment, if any, and nature of the pathological or malignant cell proliferative disorder. The effective delivery system useful in the method of the present invention may be employed in such forms as capsules, tablets, liquid solutions, suspensions, or elixirs, for oral administration or sterile liquid forms such as solutions, suspensions, or emulsions. Any inert carrier is preferably used, such as saline, or phosphate-buffered saline, or any such carrier in which the compounds used in the method of the present invention have suitable solubility properties.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the DNA or RNA constructs of the present invention may be administered as long as it has a biologically inhibiting effect on the proliferation of the treated cells. Moreover, it is possible to administer more than one of the DNA or RNA constructs of the present invention simultaneously to the same site. By "biologically inhibiting" is meant partial or total growth inhibition as well as decreases in the rate of proliferation or growth of the cells. The biologically inhibitory dose may be determined by assessing the effects of the sample DNA or RNA constructs of the present invention on target malignant or abnormally proliferating cell growth in tissue culture, tumor growth in animals and cell cultures, or any other method known to one of ordinary skill in the art. The present invention is further directed to antibody-based therapies which involve administering an anti-HOIPS I antibody to a mammalian, preferably human, patient for treating one or more of the above-described disorders. Methods for producing anti-HOIPS I polyclonal and monoclonal antibodies are described in detail supra. Such antibodies may be provided in pharmaceutically acceptable compositions as known in the art or as described herein.

A summary of the ways in which the antibodies of the present invention may be used therapeutically includes binding HOIPS I locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The pharmaceutical compositions of the present invention may be administered by any means that achieve their intended purpose. Amounts and regimens for the administration of antibodies, their fragments or derivatives can be determined readily by those with ordinary skill in the clinical art of treating cell proliferative diseases.

For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health and weight of the recipient, kind of concurrent treatment, if any, frequency of treatment, and the nature of the desired effect.

Compositions within the scope of this invention include all compositions wherein the antibody, fragment or derivative is contained in an amount effective to achieve its intended purpose. While individual needs vary, determination of optimal ranges of effective amounts of each component is within the skill of the art. The effective dose is a function of the individual chimeric or monoclonal antibody, the presence and nature of a conjugated therapeutic agent (see below), the patient and his clinical status, and can vary from about 10 µg/kg body weight to about 5000 mg/kg body weight. The preferred dosages comprise 0.1–500 mg/kg body wt.

In addition to the pharmacologically active compounds, the new pharmaceutical compositions may contain suitable pharmaceutically acceptable carriers comprising excipients and auxiliaries which facilitate processing of the active compounds into preparations which can be used pharmaceutically. Preferably, the preparations contain from about 0.01 to 99 percent, preferably from about 20–75 percent of active compound(s), together with the excipient.

Similarly, preparations of an anti—HOIPS I antibody, or antigen binding fragment thereof, of the present invention for parenteral administration, such as in detectably labeled form for imaging or in a free or conjugated form for therapy, include sterile aqueous or non-aqueous solutions, suspensions, or emulsions. Examples of non-aqueous solvents are propylene glycol, polyethylene glycol, vegetable oil, such as olive oil, and injectable organic esters such as ethyl oleate. Aqueous carriers include water, alcoholic/aqueous solutions, emulsions or suspensions, including saline and buffered media, parenteral vehicles including sodium chloride solution, Ringer's dextrose, dextrose and sodium chloride, lactated Ringer's, or fixed oils. Intravenous vehicles include fluid and nutrient replenishers, such as those based on Ringer's dextrose, and the like. Preservatives and other additives may also be present, such as, for example, antimicrobials, anti-oxidants, chelating agents, and inert gases and the like. See, generally, *Remington's Pharmaceutical Science*, 16th ed., Mack Publishing Co., Easton, Pa., 1980.

In particular, the antibodies, fragments and derivatives of the present invention are useful for treating a subject having or developing HOIPS I related cell proliferative and/or differentiation disorders as described herein. Such treatment comprises administering a single or multiple doses of the antibody, or a fragment, derivative, or a conjugate thereof The antibodies of this invention may be advantageously utilized in combination with other monoclonal or chimeric antibodies, or with lymphokines or hematopoietic growth factors, etc., which serve to increase the number or activity of effector cells which interact with the antibodies.

It is preferred to use high affinity and/or potent in vivo HOIPS I inhibiting and/or neutralizing antibodies, fragments or regions thereof, for both HOIPS I immunoassays and therapy of HOIPS I related disorders. Such antibodies, fragments, or regions, will preferably have an affinity for human HOIPS I, expressed as Ka, of at least $10^8$ M$^{-1}$, more preferably, at least $10^9$ M$^{-1}$, such as $5 \times 10^8$ M$^{-1}$ $8 \times 10^8$ M$^{-1}$, $2 \times 10^9$ M$^{-1}$, $4 \times 10^9$ M$^{-1}$, $6 \times 10^9$ M$^{-1}$, $8 \times 10^9$ M$^{-1}$.

Preferred for human therapeutic use are high affinity murine and murine/human or human/human chimeric antibodies, and fragments, regions, and derivatives thereof having potent in vivo HOIPS I inhibiting and/or neutralizing activity, according to the present invention, e.g., that block HOIPS I activity.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a HOIPS I protein gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15–25 bp) from the cDNA. Computer analysis of the 3' untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from cDNA as short as 50 or 60 bp. For a review of this technique, see Verma et al., *Human Chromosomes: A Manual Of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Thus, in one embodiment of the present invention these techniques can be used to identify individuals who are predisposed to cell proliferative diseases. Specifically, the present inventions can be used to screen chromosomal DNA of an individual to determine the presence or absence of active alleles of the HOIPS I gene. Those having only one active allele of the HOIPS I gene are predicted to be predisposed to cell proliferative disorders.

Having generally described the invention, the same will be more readily understood by reference to the following examples, which are provided by way of illustration and are not intended as limiting.

EXAMPLES

Example 1

Expression and Purification of HOIPS I in *E. coli*

The DNA sequence encoding the mature HOIPS I protein in the deposited cDNA clone is amplified using PCR oligonucleotide primers specific to the amino terminal sequences of the HOIPS I protein and to vector sequences 3' to the gene. Additional nucleotides containing restriction sites to facilitate cloning are added to the 5' and 3' sequences respectively.

The 5' oligonucleotide primer has the sequence: 5' GACTCCATGGGGCGGTGGGAAAGCCTG 3' (SEQ ID NO:4) containing the underlined NcoI restriction site, which encodes 20 nucleotides of the HOIPS I protein coding sequence in FIGS. 1A–1B (SEQ ID NO: 1) beginning immediately after the signal peptide.

The 3' primer has the sequence: 5' GACTAGATCTGAGCACATGATAGTAGCAT 3' (SEQ ID NO:5) containing the underlined BglII restriction site followed by 20 nucleotides complementary to the last 20 nucleotides of the HOIPS I protein coding sequence in FIGS. 1A–1B.

The restriction sites are convenient to restriction enzyme sites in the bacterial expression vector nQE60, which are used for bacterial expression in these examples. (Qiagen, Inc. 9259 Eton Avenue, Chatsworth, Calif., 9131 1). nQE60 encodes ampicillin antibiotic resistance ("Amp") and contains a bacterial origin of replication ("ori"), an IPTG inducible promoter, a ribosome binding site ("RBS"), a 6-His tag and restriction enzyme sites.

The amplified HOIPS I DNA and the vector nQE60 both are digested with NcoI and BglII and the digested DNAs are then ligated together. Insertion of the HOIPS I protein DNA into the restricted nQE60 vector places the HOIPS I protein coding region downstream of and operably linked to the vector's IPTG-inducible promoter and in-frame with an initiating AUG appropriately positioned for translation of HOIPS I protein.

The ligation mixture is transformed into competent $E.\ coli$ cells using standard procedures. Such procedures are described in Sambrook et al., MOLECULAR CLONING: A LABORATORY MANUAL, 2nd Ed.; Cold Spring Harbor Laboratory Press, Cold Spring Harbor, N.Y. (1989). $E.\ coli$ strain M15/rep4, containing multiple copies of the plasmid pREP4, which expresses lac repressor and confers kanamycin resistance ("Kan"'"), is used in carrying out the illustrative example described herein. This strain, which is only one of many that are suitable for expressing HOIPS I protein, is available commercially from Qiagen.

Transformants are identified by their ability to grow on LB plates in the presence of ampicillin and kanamycin. Plasmid DNA is isolated from resistant colonies and the identity of the cloned DNA confirmed by restriction analysis.

Clones containing the desired constructs are grown overnight ("O/N") in liquid culture in LB media supplemented with both ampicillin (100 μg/ml) and kanamycin (25 μg/ml).

The O/N culture is used to inoculate a large culture, at a dilution of approximately 1:100 to 1:250. The cells are grown to an optical density at 600 nm ("OD600") of between 0.4 and 0.6. Isopropyl-B-D-thiogalactopyranoside ("IPTG") is then added to a final concentration of 1 mM to induce transcription from lac repressor sensitive promoters, by inactivating the lacI repressor. Cells subsequently are incubated further for 3 to 4 hours. Cells then are harvested by centrifugation and disrupted, by standard methods. Inclusion bodies are purified from the disrupted cells using routine collection techniques, and protein is solubilized from the inclusion bodies into 8M urea. The 8M urea solution containing the solubilized protein is passed over a PD-10 column in 2× phosphate-buffered saline ("PBS"), thereby removing the urea, exchanging the buffer and refolding the protein. The protein is purified by a further step of chromatography to remove endotoxin. Then, it is sterile filtered. The sterile filtered protein preparation is stored in 2×PBS at a concentration of 95 μ/ml.

Example 2

Cloning and Expression of HOIPS I protein in a Baculovirus Expression System

In this illustrative example, the plasmid shuttle vector pA2 is used to insert the cloned DNA encoding the complete protein, including its naturally associated secretary signal (leader) sequence, into a baculovirus to express the mature HOIPS I protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from $E.\ coli$ under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39.

The cDNA sequence encoding the full length HOIPS I protein in the deposited clone, including the AUG initiation codon and the naturally associated leader sequence shown in FIGS. 1A–1B (SEQ ID NO:2), is amplified using PCR oligonucleotide primers corresponding to the 5' and 3' sequences of the gene. The 5' primer has the sequence 5' GAC TGGATCCGCC ATC ATG AAG GGT TTC ACA GCC AC 3' (SEQ ID NO:6) containing the underlined BamHI restriction enzyme site, an efficient signal for initiation of translation in eukaryotic cells, as described by Kozak, M., *J. Mol. Biol.* 196:947–950 (1987), followed by 20 bases of the sequence of the complete HOIPS I protein shown in FIGS. 1A–1B, beginning with the AUG initiation codon. The 3' primer has the sequence 5' GAC GGTACGAG-CAGCTGCACTCTTTGGG 3' (SEQ ID NO: 7) containing the underlined, Asp718 restriction site followed by 19 nucleotides complementary to the 3' noncoding sequence in FIGS. 1A–1B.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel. This fragment is designated herein "F1".

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. $E.\ coli$ HB101 or other suitable $E.\ coli$ hosts such as XL-1 Blue (Stratagene Cloning Systems, La Jolla, Calif.) cells are transformed with the ligation mixture and spread on culture plates. Bacteria are identified that contain the plasmid with the human HOIPS I gene using the PCR method, in which one of the primers that is used to amplify the gene and the second primer is from well within the vector so that only those bacterial colonies containing the HOIPS I gene fragment will show amplification of the DNA. The sequence of the cloned fragment is confirmed by DNA sequencing. This plasmid is designated herein pBacHOIPS I.

Five μg of the plasmid pBacHOIPS I is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84:7413–7417 (1987). 1 µg of BaculoGold™ virus DNA and 5 µg of the plasmid pBacHOIPS I are mixed in a sterile well of a microtiter plate containing 50 µl of serum-free Grace's medium (Life Technologies Inc., Gaithersburg, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10). After appropriate incubation, blue stained plaques are picked with the tip of a micropipettor (e.g., Eppendorf). The agar containing the recombinant viruses is then resuspended in a microcentrifuge tube containing 200 µl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-HOIPS I.

To verify the expression of the gene, Sf9 cells are grown in Grace's medium supplemented with 10% heat-inactivated FBS. The cells are infected with the recombinant baculovirus V-HOIPS I at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 µCi of $^{35}$S-methionine and 5 µCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC67109). Mammalian host cells that could be used include, human Hela 293, H9 and Jurkat cells, mouse NIH3T3 and C127 cells, Cos 1, Cos 7 and CV 1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438–447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pHOIPS I HA, is made by cloning a cDNA encoding HOIPS I into the expression vector pcDNAI/Amp or pcDNAIII (which can be obtained from Invitrogen, Inc.).

The expression vector pcDNAI/amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the HOIPS I is cloned into the polylinker region of the vector so that recombinant protein expression is directed by the CMV promoter. The plasmid construction strategy is as follows. The HOIPS I cDNA of the deposited clone is amplified using primers that contain convenient restriction sites, much as described above for construction of vectors for expression of HOIPS I in E. coli. Suitable primers include the following, which are used in this example. The 5' primer, containing the underlined HindIII site, an AUG start codon and 6 codons of the 5' coding region of the complete HOIPS I polypeptide has the following sequence: 5' AGCT AAGCTTCCGCCACCATGAAGGGTTTCACAGCC 3' (SEQ ID NO:8). The 3' primer, containing the underlined XhoI site, a stop codon, and 22 bp of 3' coding sequence has the following sequence: 5' CAGT CTCGAGTTAAGCGTAGTCTGGGACGTCGTATGGGT AGGAGCA CATGATAGTAGCATTG 3' (SEQ ID NO:9).

The PCR amplified DNA fragment and the vector, pcDNAI/Amp, are digested with HindIII and XhoI and then ligated. The ligation mixture is transformed into E. coli strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the HOIPS I-encoding fragment.

For expression of recombinant HOIPS I, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, New York (1989). Cells are incubated under conditions for expression of HOIPS I by the vector.

Expression of the HOIPS I-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, New York (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(*b*)

Cloning and Expression in CHO Cells

The vector pC4 is used for the expression of HOIPS I protein. Plasmid pC4 is a derivative of the plasmid pSV2-dhfr (ATCC Accession No. 37146). The plasmid contains the mouse DHFR gene under control of the SV40 early promoter. Chinese hamster ovary—or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimke, R. T., 1978, *J Biol. Chem.* 253:1357–1370, Hamlin, J. L. and Ma, C. 1990, *Biochem. et Biophys. Acta*, 1097:107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are BamHI, XbaI, and Asp718 restriction enzyme cleavage sites that allow integration of the gene. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the HOIPS I in a regulated way in mammalian cells (Gossen, M., & Bujard, H. 1992, *Proc. Natl. Acad. Sci. USA* 89: 5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzyme BamHI and then dephosphorylated using calf intestinal phosphatase by procedures known in the art. The vector is then isolated from a 1% agarose gel.

The DNA sequence encoding the complete HOIPS I protein including its leader sequence is amplified using PCR oligonucleotide primers corresponding to the 5' and 3' sequences of the gene. The 5' primer has the sequence 5' GACT GGATCCGCCATCATGAAGGGTTTCACAGCCAC 3' (SEQ ID NO:6) containing the underlined BamHI restriction enzyme site followed by an efficient signal for initiation of translation in eukaryotes, as described by Kozak, M.,*J. Mol. Biol.* 196:947–950 (1987), and 20 bases of the coding sequence of HOIPS I shown in FIGS. 1A–1B (SEQ ID NO:1). The 3' primer has the sequence 5' GACT GGTACCAGCAGCTGCACTCTTTGGG 3' (SEQ ID NO:10) containing the underlined Asp718 restriction site followed by 19 nucleotides complementary to the non-translated region of the HOIPS I gene shown in FIGS. 1A–1B (SEQ ID NO:1).

The amplified fragment is digested with the endonucleases BamHI and Asp718 and then purified again on a 1% agarose gel. The isolated fragment and the dephosphorylated vector are then ligated with T4 DNA ligase. E. coli HB 101 or XL- 1 Blue cells are then transformed and bacteria are identified that contain the fragment inserted into plasmid pC4 using, for instance, restriction enzyme analysis.

Chinese hamster ovary cells lacking an active DHFR gene are used for transfection. 5 μg of the expression plasmid pC4 is cotransfected with 0.5 μg of the plasmid pSV2-neo using lipofectin (Feigner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/mil G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 mM, 20 mM). The same procedure is repeated until clones are obtained which grow at a concentration of 100–200 μM. Expression of the desired gene product is analyzed, for instance, by SDS-PAGE and Western blot or by reverse phase HPLC analysis.

Example 4

Tissue Distribution of HOIPS I mRNA Expression

Northern blot analysis is carried out to examine HOIPS I gene expression in human tissues, using methods described by, among others, Sambrook et al., cited above. A cDNA probe containing the entire nucleotide sequence of the HOIPS I protein (SEQ ID NO: 1) is labeled with $^{32}P$ using the rediprime™ DNA labeling system (Amersham Life Science), according to manufacturer's instructions. After labeling, the probe is purified using a CHROMA SPIN-100™ column (Clontech Laboratories, Inc.), according to manufacturer's protocol number PT1200-1. The purified labeled probe is then used to examine various human tissues for HOIPS I mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT 1190-1. Following hybridization and washing, the blots are mounted and exposed to film at −70° C. overnight, and films developed according to standard procedures.

The HOIPS I gene has been found to be expressed in hematopoetic tissues including: spleen, tonsils, bone marrow, dendritic cells, fetal and adult brain macrophages, B cells, lymph nodes etc.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

What is claimed is:

1. An isolated polynucleotide comprising a nucleic acid encoding amino acids 1 to 142 of SEQ ID NO:2.

2. The isolatedpolynucleotide of claim 1, comprising nucleotides 80 to 505 of SEQ ID NO:1.

3. The isolated polynucleotide of claim 1, comprising a nucleic acid encoding amino acids −19 to 142 of SEQ ID NO:2.

4. The isolated polynucleotide of claim 3, comprising nucleotides 23 to 505 of SEQ ID NO:1.

5. The isolated polynucleotide of claim 1, comprising a nucleic acid encoding amino acids −20 to 142 of SEQ ID NO:2.

6. The isolated polynucleotide of claim 5, comprising nucleotides 20 to 505 of SEQ ID NO:1.

7. The isolated polynucleotide of claim 1, which is DNA.

8. The isolated polynucleotide of claim 1, which is RNA.

9. The isolated polynucleotide of claim 1, further comprising a heterologous polynucleotide.

10. A method of producing a vector that comprises inserting the isolated polynucleotide of claim 1 into a vector.

11. A vector comprising the isolated polynucleotide of claim 1.

12. The vector of claim 11, wherein said polynucleotide is operably associated with a heterologous regulatory sequence.

13. A host cell comprising the isolated polynucleotide of claim 1.

14. The host cell of claim 13, wherein said isolated polynucleotide is operably associated with a heterologous regulatory sequence.

15. A method of producing a polypeptide that comprises culturing the host cell of claim 14 under conditions such that said polypeptide is expressed, and recovering said polypeptide.

16. A composition comprising the isolated polynucleotide of claim 1.

17. An isolated polynucleotide comprising a nucleic acid encoding the mature polypeptide encoded by the cDNA clone contained in ATCC Deposit No. 97825.

18. The isolated polynucleotide of claim 17, comprising a nucleic acid encoding the complete polypeptide encoded by the cDNA contained in ATCC Deposit No. 97825.

19. The isolated polynucleotide of claim 17, which is DNA.

20. The isolated polynucleotide of claim 17, which is RNA.

21. The isolated polynucleotide of claim 17, further comprising a heterologous polynucleotide.

22. A method of producing a vector that comprises inserting the isolated polynucleotide of claim 17 into a vector.

23. A vector comprising the isolated polynucleotide of claim 17.

24. The vector of claim 23, wherein said polynucleotide is operably associated with a heterologous regulatory sequence.

25. An isolated polynucleotide comprising 24 contiguous nucleotides of the coding region of SEQ ID NO:1 or the complement thereof, wherein said isolated polynucleotide does not comprise any one of SEQ ID NOs:12–16.

26. The isolated polynucleotide of claim 25, comprising 50 contiguous nucleotides of the coding region of SEQ ID NO:1 or the complement thereof.

27. The isolated polynucleotide of claim 26, comprising 100 contiguous nucleotides of the coding region of SEQ ID NO:1 or the complement thereof.

28. The isolated polynucleotide of claim 27, comprising 250 contiguous nucleotides of the coding region of SEQ ID NO:1 or the complement thereof.

29. The isolated polynucleotide of claim 25, comprising a nucleic acid encoding a fragment of SEQ ID NO:2, wherein said fragment binds to an antibody which binds to a polypeptide consisting of amino acids 1 to 142 of SEQ ID NO:2.

30. The isolated polynucleotide of claim 25, which is DNA.

31. The isolated polynucleotide of claim 25, which is RNA.

32. The isolated polynucleotide of claim 25, further comprising a heterologous polynucleotide.

33. A method of producing a vector that comprises inserting the isolated polynucleotide of claim 25 into a vector.

34. A vector comprising the isolated polynucleotide of claim 25.

35. The vector of claim 34, wherein said polynucleotide is operably associated with a heterologous regulatory sequence.

36. A host cell comprising the isolated polynucleotide of claim 25.

37. The host cell of claim 36, wherein said isolated polynucleotide is operably associated with a heterologous regulatory sequence.

38. A method of producing a polypeptide that comprises culturing the host cell of claim 36 under conditions such that said polypeptide is expressed, and recovering said polypeptide.

39. A composition comprising the isolated polynucleotide of claim 25.

40. A host cell comprising the isolated polynucleotide of claim 17.

41. The host cell of claim 40, wherein said isolated polynucleotide is operably associated with a heterologous regulatory sequence.

42. A method of producing a polypeptide that comprises culturing the host cell of claim 40 under conditions such that said polypeptide is expressed, and recovering said polypeptide.

43. A composition comprising the isolated polynucleotide of claim 17.

44. An isolated polynucleotide, comprising a nucleic acid which encodes an amino acid sequence selected from the group consisting of:
   (a) amino acids −4 to 9 of SEQ ID NO:2, wherein said polynucleotide does not comprise SEQ ID NO:12;
   (b) amino acids 13 to 19 of SEQ ID NO:2,
   (c) amino acids 23 to 32 of SEQ ID NO:2, wherein said polynucleotide does not comprise SEQ ID NO:12 or SEQ ID NO:15;
   (d) amino acids 36 to 47 of SEQ ID NO:2, wherein said polynucleotide does not comprise SEQ ID NO:12, SEQ ID NO:15 or SEQ ID NO:16;
   (e) amino acids 54 to 63 of SEQ ID NO:2, wherein said polynucleotide does not comprise SEQ ID NO:12 or SEQ ID NO:16;
   (f) amino acids 90 to 100 of SEQ ID NO:2, wherein said polynucleotide does not comprise SEQ ID NO:12, SEQ ID NO:13 or SEQ ID NO:14;
   (g) amino acids 105 to 119 of SEQ ID NO:2, wherein said polynucleotide does not comprise SEQ ID NO:13 or SEQ ID NO:14; and
   (h) amino acids 125 to 132 of SEQ ID NO:2, wherein said polynucleotide does not comprise SEQ ID NO:12, SEQ ID NO:13 or SEQ ID NO:14.

45. The isolated polynucleotide of claim 44, wherein said amino acid sequence is (a).

46. The isolated polynucleotide of claim 44, wherein said amino acid sequence is (b).

47. The isolated polynucleotide of claim 44, wherein said amino acid sequence is (c).

48. The isolated polynucleotide of claim 44, wherein said amino acid sequence is (d).

49. The isolated polynucleotide of claim 44, wherein said amino acid sequence is (e).

50. The isolated polynucleotide of claim 44, wherein said amino acid sequence is (f).

51. The isolated polynucleotide of claim 44, wherein said amino acid sequence (g).

52. The isolated polynucleotide of claim 44, which is DNA.

53. The isolated polynucleotide of claim 44, which is RNA.

54. The isolated polynucleotide of claim 44, further comprising a heterologous polynucleotide.

55. A method of producing a vector that comprises inserting the isolated polynucleotide of claim 44 into a vector.

56. A vector comprising the isolated polynucleotide of claim 44.

57. The vector of claim 56, wherein said isolated polynucleotide is operably associated with a heterologous regulatory sequence.

58. A host cell comprising the isolated polynucleotide of claim 44.

59. The host cell of claim 58, wherein said polynucleotide is operably associated with a heterologous regulatory sequence.

60. A method of producing a polypeptide that comprises culturing the host cell of claim 58 under conditions such that said polypeptide is expressed, and recovering said polypeptide.

61. A composition comprising the isolated polynucleotide of claim 44.

62. An isolated polynucleotide comprising a first nucleic acid 95% or more identical to a reference nucleic acid encoding an amino acid sequence selected from the group consisting of:
   (a) amino acids −20 to 142 of SEQ ID NO:2;
   (b) amino acids −19 to 142 of SEQ ID NO:2;
   (c) amino acids 1 to 142 of SEQ ID NO:2;
   (d) the amino acid sequence of the mature polypeptide encoded by the cDNA clone contained in ATCC Deposit No. 97825; and
   (e) the amino acid sequence of the complete polypeptide encoded by the cDNA clone contained in ATCC Deposit No. 97825;
wherein percent identity is calculated using Bestfit with the parameters set such that percentage of identity is calculated over the full length of the reference nucleic acid and that gaps in homology of up to 5% of the total number of nucleotides in the reference nucleic acid are allowed.

63. An isolated polynucleotide comprising a nucleic acid encoding an amino acid sequence, wherein, except for one to thirty conservative amino acid substitutions, said amino acid sequence is selected from the group consisting of:
   (a) amino acids −20 to 142 of SEQ ID NO:2;
   (b) amino acids −19 to 142 of SEQ ID NO:2;
   (c) amino acids 1 to 142 of SEQ ID NO:2;
   (d) the amino acid sequence of the mature polypeptide encoded by the cDNA clone contained in ATCC Deposit No. 97825; and
   (e) the amino acid sequence of the complete polypeptide encoded by the cDNA clone contained in ATCC Deposit No. 97825.

64. The isolated polynucleotide of claim 63, wherein the number of substitutions is not more than 10.

65. The isolated polynucleotide of claim 64, wherein the number of substitutions is not more than 5.

66. The isolated polynucleotide of claim 65, wherein the number of substitutions is not more than 3.

67. An isolated polynucleotide comprising a nucleic acid encoding an amino acid sequence 95% or more identical to a reference amino acid sequence selected from the group consisting of:
   (a) amino acids −20 to 142 of SEQ ID NO:2;
   (b) amino acids −19 to 142 of SEQ ID NO:2;
   (c) amino acids 1 to 142 of SEQ ID NO:2;

(d) the amino acid sequence of the mature polypeptide encoded by the cDNA clone contained in ATCC Deposit No. 97825; and (e) the amino acid sequence of the complete polypeptide encoded by the cDNA clone contained in ATCC Deposit No. 97825;

wherein percent identity is calculated using Bestfit with the parameters set such that percentage of identity is calculated over the full length of the reference amino acid sequence and that gaps in homology of up to 5% of the total number of amino acids in the reference amino acid sequence are allowed.

68. An isolated polynucleotide comprising a nucleic acid which is 95% or more identical to a reference nucleic acid, wherein said reference nucleic acid is selected from the group consisting of:

(a) nucleotides 80 to 505 of SEQ ID NO:1;
(b) nucleotides 23 to 505 of SEQ ID NO:1; and
(c) nucleotides 20 to 505 of SEQ ID NO:1;

wherein percent identity is calculated using Bestfit with the parameters set such that percentage of identity is calculated over the full length of the reference nucleic acid and that gaps in homology of up to 5% of the total number of nucleotides in the reference nucleic acid are allowed.

69. An isolated polynucleotide comprising a first nucleic acid which hybridizes (i) at 42° C. in a solution consisting of 50% formamide, 5×SSC, 50 mM sodium phosphate, 5×Denhardt's solution, 10% dextran sulfate, and 20 µg/ml denatured, sheared salmon sperm DNA; (ii) followed by washing in a solution consisting of 0.1×SSC at 65° C.; to a second nucleic acid having the nucleotide sequence of the coding region of SEQ ID NO:1 or the complement thereof; wherein said first nucleic acid is 15 or more nucleotides long and provided that said isolated polynucleotide does not comprise any one of SEQ ID NOs:12–16.

* * * * *